United States Patent [19]

Mitamura et al.

[11] Patent Number: 5,081,252

[45] Date of Patent: Jan. 14, 1992

[54] PROCESS FOR THE PREPARATION OF AROMATIC CARBOXYLIC ACIDS

[75] Inventors: Shuichi Mitamura; Yoshimi Kata; Koichi Fujishiro; Yasuhisa Tsutsumi, all of Kanagawa, Japan

[73] Assignees: Nippon Steel Corporation; Nippon Steel Chemical Co., Ltd., both of Tokyo, Japan

[21] Appl. No.: 361,180

[22] Filed: Jun. 5, 1989

[30] Foreign Application Priority Data

Jun. 6, 1988 [JP] Japan ................................ 63-137389
Nov. 7, 1988 [JP] Japan ................................ 63-279437

[51] Int. Cl.$^5$ ................. C07D 219/04; C07D 209/82; C07D 355/04
[52] U.S. Cl. ..................................... 546/102; 546/147; 546/170; 546/315; 546/326; 548/441; 548/492; 548/531; 548/532; 548/533; 549/23; 549/484; 549/485; 549/486; 549/468; 549/58; 562/480; 562/490; 562/493
[58] Field of Search ....................... 562/480, 490, 493; 548/441, 492, 531, 532, 533; 549/484, 485, 486, 468, 58, 23; 546/170, 147, 102, 315, 326

[56] References Cited

U.S. PATENT DOCUMENTS

| 2,823,231 | 2/1958 | Raecke et al. | |
| 3,023,216 | 2/1962 | Blaser et al. | 260/295.5 |
| 3,043,846 | 7/1962 | Blaser et al. | 260/295 |

FOREIGN PATENT DOCUMENTS

| 0217329A1 | 4/1987 | European Pat. Off. | |
| 1056598 | 5/1959 | Fed. Rep. of Germany | |
| 3148987 | 12/1980 | Fed. Rep. of Germany | 260/295 |
| 45-7737 | 3/1970 | Japan | |

OTHER PUBLICATIONS

Raecke, B., "Synthese von Di-und Tricarbonsäuren Aromatischer Ringsysteme durch Verschiebung von Carboxyl-Gruppen", *Angewandte Chemie*, vol. 70, No. 1 (Jan. 7, 1958), pp. 1-5.
Raecke, B., et al., "2,6-Naphthalenedicarboxylic Acid", *Organic Synthesis*, vol. 5 (1973), pp. 813-817.
Yamashita, Junzo et al., "Studies on Aromatic Carboxylic Acids II; Synthesis of 2,6-Naphthalenedicarboxylic Acid by Henkel Process", *Organic Synthetic Chemistry*, vol. 20, No. 5 (1962), pp. 501-506.
McNelis, Edward; "Reactions of Aromatic Carboxylates, II, The Henkel Reaction", *Journal of Organic Chemistry*, vol. 30 (1965), pp. 1209-1213.

*Primary Examiner*—Johann Richter
*Attorney, Agent, or Firm*—Armstrong, Nikaido, Marmelstein, Kubovcik & Murray

[57] ABSTRACT

A process for the preparation of aromatic carboxylic acids or their salts comprises heating carboxyl-free aromatic compounds and aromatic carboxylic acid salts whose basic structures differ from those of the aromatic compounds, or heating polycyclic aromatic compounds with three or more rings and monocyclic or bicyclic aromatic carboxylic acid salts, under carbon dioxide pressure in the presence of one or more metal compounds selected from group (a) of compounds of zinc, cadmium, and thallium and one or more compounds selected from group (b) of compounds of cesium, Group II metals, And Group IIIa metals to effect the intermolecular transfer of the carboxyl groups.

11 Claims, No Drawings

PROCESS FOR THE PREPARATION OF AROMATIC CARBOXYLIC ACIDS

FIELD OF THE INVENTION AND RELATED ART STATEMENT

This invention relates to a process for the preparation of aromatic carboxylic acids or their salts by utilizing the intermolecular transfer of the carboxyl groups.

The aromatic carboxylic acid salts can be converted with ease to the corresponding free acids by acidification. 2,6-Naphthalenedicarboxylic acid, a typical aromatic carboxylic acid, has been recognized in recent years as a compound of industrial value useful for an acid moiety of polyesters.

A large number of processes have been proposed for the preparation of aromatic carboxylic acids or their salts. Examples of representative processes are described below with respect to the preparation of a di(alkali metal) salt of 2,6-naphthalenedicarboxylic acid.

One is the so-called Henkel process. According to this process, an alkali metal salt of a naphthoic acid or a di(alkali metal) salt of a naphthalenedicarboxylic acid or a mixture thereof is heated with a catalyst under carbon dioxide pressure at or above 350° C., normally in the range of 400° to 500° C. The alkali metal salt of a naphthoic acid disproportionates to di(alkali metal) 2,6-naphthalenedicarboxylate and naphthalene while the di(alkali metal) naphthalenedicarboxylate rearranges selectively to di(alkali metal) 2,6-naphthalenedicarboxylate. Reference should be made to the following literature: (1) B. Raecke, Angew. Chem., 70, 1 (1958); (2) B. Raecke et al., Org. Syn. Coll., 5, 813 (1973); (3) Yamashita et al., Journal of Synthetic Organic Chemistry, Japan, 20, 501 (1962); (4) E. McNelis, J. Org. Chem., 30, 1209 (1965); (5) U.S. Pat. No. 2,823,231; (6) Japanese Tokkyo Kokoku Koho No. 51-10,224 (1976); and (7) EP 0 217 329 A1.

An alternative process disclosed in Federal Republic of Germany Patent 1,056,598 prepares the desired salt by heating pyromellitic acid tetrapotassium salt, naphthalene, aluminum carbide, and cadmium chloride in carbon dioxide pressurized to 1,450 atmospheres at 425° C. for 15 hours.

The former process uses alkali metal naphthoates or di(alkali metal) naphthalenedicarboxylates or a mixture thereof as raw materials. These salts, however, are not readily available and costly.

The latter process, on the other hand, requires an extremely high pressure of 1,450 atmospheres for the reaction. This incurs an enormous cost for high-pressure equipment and increases operational hazards when the process is run on an industrial scale.

OBJECT AND SUMMARY OF THE INVENTION

An object of this invention is to provide a process for the preparation of aromatic carboxylic acids which is capable of solving the aforesaid problems associated with the conventional processes, namely costly raw materials and mandatory use of the high-pressure reaction.

Another object of this invention is to provide a process for the preparation of aromatic carboxylic acids from inexpensive raw materials in an industrially operable low-pressure reaction.

A further object of this invention is to provide a process for the preparation of aromatic carboxylic acids or their salts in high yields under relatively mild reaction conditions using as a catalyst one or more metal compounds selected from group (a) of compounds of zinc, cadmium, and thallium and one or more compounds selected from group (b) of compounds of cesium, Group II a metals, and Group III a metals.

A still further object of this invention is to provide a process for the preparation of novel polycyclic aromatic carboxylic acids or their salts by the reaction under heat of carboxyl-free polycyclic aromatic compounds containing three or more rings with aromatic carboxylic acid salts containing one or two rings under carbon dioxide pressure in the presence of one or more metal compounds selected from group (a) of compounds of zinc, cadmium, and thallium or one or more metal compounds of group (a) together with one or more compounds selected from group (b) of compounds of cesium, Group II a metals, and Group III a metals as catalyst.

Accordingly, this invention relates to a process for the preparation of aromatic carboxylic acids or their salts by the reaction under heat of carboxyl-free aromatic compounds with aromatic carboxylic acid salts under carbon dioxide pressure in the presence of a catalytic amount of one or more metal compounds selected from group (a) of compounds of zinc, cadmium, and thallium and one or more compounds selected from group (b) of compounds of cesium, Group II a metals, and Group III a metals.

Furthermore, this invention relates to a process for the preparation of polycyclic aromatic carboxylic acids or their salts by the reaction under heat of carboxyl-free polycyclic aromatic compounds containing three or more rings with aromatic carboxylic acid salts containing one or two rings under carbon dioxide pressure in the presence of a catalytic amount of one or more metal compounds selected from group (a) of compounds of zinc, cadmium, and thallium.

The carboxyl-free aromatic compounds (hereinafter referred to as Ar) to be used as raw material in the process of this invention are aromatic compounds, preferably polycyclic, which possess one or more substitutable hydrogen atoms bonded to the aromatic ring. Examples of such aromatic compounds include naphthalene, biphenyl, phenanthrene, anthracene, indene, pyrene, terphenyl, diphenylmethane, diphenyl ether, indole, quinoline, isoquinoline, carbazole, acridine, thionaphthene, diphenylene oxide, acenaphthene, fluorene, benzofuran, dibenzothiophene, furan, thiophene, pyridine, and pyrrole. The aromatic carboxylic acid salts (hereinafter referred to as B—C) to be used as co-raw material in the process of this invention may be any of aromatic compounds containing one or more carboxylic groups, preferably benzenecarboxylic acid alkali metal salts, more preferably alkali metal salts of benzenepolycarboxylic acids with two or more carboxyl groups. Examples of B—C include salts, applied either singly or mixed, of benzenecarboxylic acids such as benzoic acid, phthalic acid, isophthalic acid, terephthalic acid, trimellitic acid, trimesic acid, hemimellitic acid, pyromellitic acid, prehnitic acid, mellophanic acid, and benzenepentacarboxylic acid, naphthalenecarboxylic acids, and biphenylcarboxylic acids. A mixture of aforesaid aromatic carboxylic acid salts may be prepared by mixing any two or more of B—C or by the following procedure with ease. Coal or coaltar pitch is oxidized by oxygen or an oxygen-containing gas in an aqueous alkaline solution to yield with ease at low cost a mixture of aromatic carboxylic acids consisting of benzenecarboxylic acids (any or all of mono-to hexa-carboxylated) and other polycylic aromatic carboxylic acids and the acids are converted to their corresponding alkali metal salts as described, for example, by Kamiya et al., Journal of Synthetic Organic Chemistry, Japan, 17, 109 (1959). The salts may be of a variety of metals and of ammonium and those of alkali metals are advantageous. Potassium and sodium are desirable among the alkali metals and the potassium salts, in particular, yield good results.

It is also possible to prepare B—C by adding a metal salt to an aromatic carboxylic acid anhydride under the reaction conditions. This invention comprises the use of aromatic carboxylic acid anhydrides and metal salts as starting materials. Similarly, it is possible to produce a carboxylic acid salt from an aromatic carboxylic acid and an alkali; however, this route is undesirable as water simultaneously formed in the reaction system hinders the reaction.

It is necessary for Ar to differ in the basic structure from B—C stripped of the carboxyl groups and the Ar desirably form more chemically stable carboxylated aromatic compounds (hereinafter referred to as Ar—C). The amount of B—C to be used is 0.01 to 2 times in weight, preferably 0.01 to 1 times, of Ar.

The process of this invention uses as catalyst one or more metal compounds selected from group (a) of compounds of zinc, cadmium, and thallium and one or more compounds selected from group (b) of compounds of cesium, Group II a metals, and Group III a metals. In the cases where the carboxyl-free aromatic compounds are polycylic with three or more rings and the aromatic carboxylic acid salts are monocyclic or bicyclic, the catalyst may be one or more metal compounds selected from group (a) of compounds of zinc, cadmium, and thallium.

The metal compounds of zinc, cadmium, and thallium, namely metal compounds of group (a), to be used in the process of this invention include zinc halides (e.g. zinc fluoride, zinc chloride, zinc bromide, and zinc iodide), zinc oxide, zinc carbonate, and organic zinc salts (e.g. zinc phthalate and zinc naphthoate); cadmium halides (e.g. cadmium fluoride, cadmium chloride, cadmium bromide, and cadmium iodide), cadmium oxide, cadmium carbonate, and organic cadmium salts (e.g. cadmium phthalate and cadmium naphthoate); and thallium halides (e.g. thallium fluoride, thallium chloride, thallium bromide, and thallium iodide), thallium oxide, thallium carbonate, and organic thallium salts. These metal compounds may be used singly or mixed or may additionally contain a Group II b compound, namely a mercury compound such as a mercury halide (e.g. mercury fluoride, mercury chloride, mercury bromide, or mercury iodide), mercury oxide, and mercury carbonate. The amount of the metal compounds of group (a) is normally 0.5 to 30 mole %, preferably 5 to 25 mole %, of B—C. The addition in excess of 30 mole % promotes the formation of carbonized matters as by-products.

The cesium compounds to be used with the aforesaid metal compounds of group (a) in the process of this invention may be any one, or a mixture of any two or more, of cesium halides (e.g. cesium fluoride, cesium chloride, cesium bromide, and cesium iodide), cesium oxide, cesium carbonate, and organic cesium salts (e.g. cesium phthalate and cesium naphthoate).

The Group II a metal compounds to be used with the aforesaid metal compounds of group (a) may be any one, or a mixture of any two or more, of magnesium halides (e.g. magnesium fluoride, magnesium chloride, magnesium bromide, and magnesium iodide), magnesium oxide, magnesium carbonate, and organic magnesium salts (e.g. magnesium phthalate and magnesium naphthoate); calcium halides (e.g. calcium fluoride, calcium chloride, calcium bromide, and calcium iodide), calcium oxide, calcium carbonate, and organic calcium salts (e.g. calsium phthalate and calcium naphthoate); strontium halides (e.g. strontium fluoride, strontium chloride, strontium bromide, and strontium iodide), strontium oxide, strontium carbonate, and organic strontium salts (e.g. strontium phthalate and strontium naphthoate); and barium halides (e.g. barium fluoride, barium chloride, barium bromide, and barium iodide), barium oxide, barium carbonate, and organic barium salts (e.g. barium phthalate and barium naphthoate).

The Group III a metal compounds to be used with the aforesaid metal compounds of group (a) may be any one, or a mixture of any two or more, of scandium halides (e.g. scandium fluoride, scandium chloride, scandium bromide, and scandium iodide), scandium oxide, scandium carbonate, and organic scandium salts; yttrium halides (e.g. yttrium fluoride, yttrium chloride, yttrium bromide, and yttrium iodide), yttrium oxide, yttrium carbonate, and organic yttrium salts; and compounds of lanthanide metals such as lanthanum, cerium, praseodymium, neodymium, gadolinium, samarium, and ytterbium. Preferred among the lanthanide compounds are halides such as the following: lanthanum fluoride, lanthanum chloride, lanthanum bromide, lanthanum iodide, cerium fluoride, cerium chloride, cerium bromide, cerium iodide, neodymium fluoride, neodymium chloride, neodymium bromide, neodymium iodide, gadolinium fluoride, gadoliniium chloride, gadolinium bromide, gadolinium iodide, samarium fluoride, samarium chloride, samarium bromide, samarium iodide, ytterbium fluoride, ytterbium chloride, ytterbium bromide, and ytterbium iodide.

The amount of one or more compounds of cesium, Group II a metals, and Group III a metals is normally 0.5 to 30 mole %, preferably 5 to 25 mole %, of B—C. The catalytic activity is not sufficiently high with 0.5 mole % or less while the formation of carbonized matters increases with more than 30 mole %. The mole ratio of one or more metal compounds selected from group (a) of compounds of zinc, cadmium, and thallium to one or more compounds selected from group (b) of compounds of cesium, Group II a metals, and Group III a metals, or the mole ratio of the metal compound of group (a) to the compound of group (b), is desirably 0.2 to 5.

In the process of this invention, it is acceptable to add to the reaction system those compounds which promote the reaction besides the catalyst consisting of one or more metal compounds selected from group (a) of compounds of cadmium, zinc, and thallium and one or more compounds selected from group (b) of compounds of cesium, Group II a metals, and Group III a metals. Inorganic halides are desirable as such compounds. Of the inorganic halides, iodides and bromides are particularly desirable. Their examples include lithium iodide, lithium bromide, sodium iodide, sodium bromide, potassium iodide, potassium bromide, rubidium iodide, and rubidium bromide. The addition of such reaction-promoting compounds is most effective where a halide anion is absent in the reaction system, for example, when cadmium terephthalate and cesium phthalate are used as catalyst. The inorganic halides, like the catalysts, are normally added in an amount of 0.5 to 30 mole % of B—C.

Moreover, aprotic aromatic compounds with two to three rings that are less reactive than the Ar used as raw material, melt at the reaction temperature, and help to turn the reaction system into a solution or a homogeneous dispersion may be used as solvent or dispersion medium, either singly or mixed, whereby an increase in the yields of the desired aromatic carboxylic acids or their salts is attained. Preferred examples of such aprotic aromatic compounds are naphthalene, biphenyl, diaryl ethers (e.g. diphenyl ether), lower alkylnaphthalenes (e.g. methylnaphthalenes and dimethylnaphthalenes), lower alkylbiphenyls (e.g. methylbiphenyls and dimethylbiphenyls), terphenyls, anthracene, and phenanthrene.

In the process of this invention, one or more metal compounds selected from group (a) of compounds of zinc, cadmium, and thallium or one or more compounds selected from group (b) of compounds of cesium, Group II a metals, and Group III a metals to be added as catalyst to the reaction system are desirably mixed thoroughly with B—C prior to the reaction and this can be done without affecting the practice of this invention by, for example, mixing an aqueous solution of the raw materials with the catalyst and subsequently distilling off the water or pulverizing the mixture of the raw materials and the catalyst in a ball mill.

In the process of this invention, Ar and B—C are heated under carbon dioxide pressure in the presence of the aforesaid catalyst whereby the substitution of the hydrogen atoms bonded to the aromatic ring in Ar with the carboxyl groups on B—C is effected via intermolecular transfer to give carboxylic acids containing Ar as nucleus or their salts (Ar—C). Examples of Ar—C include naphthalenecarboxylic acids (e.g. 2,6-naphthalenedicarboxylic acid), biphenylcarboxylic acids (e.g. 4,4'-biphenyldicarboxylic acid), diphenylene oxide carboxylic acids (e.g. diphenylene oxide-1,3,6,8-tetracarboxylic acid), phenanthrenecarboxylic acids (e.g. phnanthrene-2,7-dicarboxylic acid), carbazolecarboxylic acids (e.g. carbozole-2,4,6,8-tetracarboxylic acid), anthracenecarboxylic acids, dibenzothiophenecarboxylic acids, quinolinecarboxylic acids, and isoquinolinecarboxylic acids, and their salts.

In the process of this invention, the pressure of carbon dioxide gas in the reaction is 10 to 200 $Kg/cm^2$. G, preferably 20 to 150 $Kg/cm^2$. G, at the prevailing reaction temperature.

The reaction temperature, although varying somewhat with the raw materials and the catalyst, is normally in the range of 300° to 500° C. and is desirably in the range of 350° to 450° C. from the viewpoint of rapid occurrence of the reaction and adequate control of secondary reactions such as the formation of carbonized matters. The reaction time varies with the reaction temperature, but ranges normally from 1 to 50 hours.

Upon completion of the reaction, water is added to the reaction mixture to dissolve the aromatic carboxylic acid salts therein contained, an organic solvent such as toluene and xylene is further added to dissolve the unchanged raw materials and the aromatic compounds formed as by-products in the reaction, the resulting mixture is separated into an aqueous layer and an organic solvent layer, and the desired products are separated from the aqueous layer. The compounds of cadmium, zinc, or thallium in the catalyst are present as oxide or carbonate, soluble in neither the water nor the organic solvent, and are separated readily along with the similarly insoluble carbonized matters by such means as filtration.

DETAILED DESCRIPTION OF THE PREFERRED EMBODIMENT

The process of this invention is explained in detail with reference to the accompanying examples and comparative examples.

EXAMPLES 1-11

Dipotassium phthalate was mixed with cadmium compound and cesium compound in the proportions shown in Table 1 and pulverized in a ball mill. An autoclave was charged with 10.0 g of the mixture and 30.0 g naphthalene, heated to 100° C., flushed with carbon dioxide gas, and filled with carbon dioxide gas to the initial pressure shown in Table 1.

TABLE 1

| | Kind and amount of cadmium compound (mol %) | | Kind and amount of cesium compound (mol %) | | Reaction pressure $(Kg/cm^2 \cdot G)$ | | Reaction temperature (°C.) | Yield (*1) (%) |
|---|---|---|---|---|---|---|---|---|
| | | | | | Initial pressure | Final Pressure | | |
| Example 1 | CdI₂ | 16 | CsI | 16 | 40 | 65 | 400 | 53 |
| Example 2 | " | " | CsBr | " | " | " | " | 52 |
| Example 3 | " | " | CsCl | " | " | " | " | 37 |
| Comparative Example 1 | " | " | — | — | " | " | " | 5 |
| Example 4 | " | " | CsI | 16 | " | 64 | 390 | 50 |
| Example 5 | " | " | " | " | " | 68 | 430 | 21 |
| Example 6 | " | " | " | " | 20 | 40 | 400 | 22 |
| Example 7 | " | 20 | " | 20 | 40 | 65 | " | 54 |
| Example 8 | " | 16 | " | 8 | " | " | " | 33 |
| Example 9 | " | 8 | " | 16 | " | " | " | 31 |
| Example 10 | " | " | " | 8 | " | " | " | 13 |
| Comparative Example 2 | " | " | — | — | " | " | " | 3 |
| Example 11 | CdCl₂ | 16 | CsI | 16 | " | 64 | " | 14 |
| Comparative Example 3 | " | " | — | — | " | " | " | 1 |

(Note)
(*1): Yield of 2,6-naphthalenedicarboxylic acid salt

The mixture in the autoclave was heated with stirring to the reaction temperature shown in Table 1 at a rate of 5° C./minute and stirred at this temperature for 18 hours. When the reaction was over, 200 ml of toluene and 200 ml of water were added to the reaction mixture, stirred well, the solids soluble in neither the water nor the toluene were filtered off, and the aqueous layer was separated. A portion of the aqueous layer was sampled and analyzed for the salt of 2,6-naphthalenedicarboxylic acid by high performance liquid chromatography with application of the internal standard method. The results are shown in Table 1. The yield of the 2,6-naphthalenedicarboxylic acid salt is calculated on the basis of the amount of B—C charged.

COMPARATIVE EXAMPLES 1-3

The reactions were carried out as in the aforesaid Examples 1-3, Example 10, and Example 11, respectively with the exception that the cesium compound was not used. The results are shown in Table 1.

EXAMPLE 12

The reaction was carried out as in Example 1 with the exception that tetrapotassium pyromellitate was substituted for the dipotassium phthalate and the zinc chloride was substituted for the cadmium iodide, and the reaction temperature was set at 430° C. The final pressure in the reaction was 68 Kg/cm$^2$. G and the analysis of the reaction products as in Example 1 indicated the production of the desired 2,6-naphthalenedicarboxylic acid salt in a yield of 8% by mole.

EXAMPLE 13

The reaction was carried out as in Example 9 with the exception that an amount of 8 mole % of the zinc iodide was used as catalyst in addition to the amount of 8 mole % of the cadmium iodide. The final pressure in the reaction was 72 Kg/cm$^2$. G and the analysis of the reaction products as in Example 1 indicated the production of the desired 2,6-naphthalenedicarboxylic acid salt in a yield of 37% by weight.

EXAMPLES 14-24

The Group II a metal or Group III a metal of group (b) shown in Table 2 was added to dipotassium phthalate in an amount of 16 mole % of the phthalate and pulverized in a ball mill to obtain a mixture of the dipotassium phthalate and the catalyst. An autoclave was charged with 10.0 g of the mixture and 30.0 g of naphthalene, heated to 100° C., flushed with carbon dioxide gas, and then filled with carbon dioxide gas to a pressure of 40 Kg/cm$^2$. G.

TABLE 2

| Example No. | Kind of catalyst (b) (*1) | Reaction temperature (°C.) | Yield (*2) |
| --- | --- | --- | --- |
| 14 | MgCl$_2$ | 400 | 7 |
| 15 | CaCl$_2$ | " | 13 |
| 16 | SrCl$_2$ | " | 18 |
| 17 | BaCl$_2$ | " | 24 |
| 18 | CeCl$_3$ | " | 26 |
| 19 | BaCl$_2$ | 380 | 19 |
| 20 | BaCl$_2$ | 430 | 8 |
| 21 | LaCl$_3$ | 400 | 29 |
| 22 | NdCl$_3$ | " | 22 |
| 23 | GdCl$_3$ | " | 16 |
| 24 | YCl$_3$ | " | 16 |

(Notes)
(*1): Kind of group IIa metal compound and IIIa compound
(*2): Yield of 2.6-naphthalenedicarboxylic acid salt The mixture in the autoclave was heated with stirring to the reaction temperature shown in Table 2 at a rate of 5° C./minute and stirred at this temperature for 18 hours. Upon completion of the reaction, 200 ml of toluene and 200 ml of water were added to the reaction mixture, stirred well, the solids soluble in neither the water nor the toluene were filtered off, and the aqueous layer was separated. A portion of the aqueous layer was analyzed as in Example 1. The results are shown in Table 2.

EXAMPLES 25-28

Dipotassium terephthalate, dipotassium isophthalate, potassium benzoate, or tetrapotassium pyromellitate was mixed with cadmium iodide and cesium iodide, each in an amount of 16 mole % of the carboxylate salt, to prepare a mixture of the aromatic carboxylic acid salt and the catalyst as in Example 1. The mixture, 10.0 g, and 30.0 g of naphthalene were submitted to the reaction at 400° C. for 18 hours and the products were separated and analyzed in a manner similar to that in Example 1. The pressure of carbon dioxide gas was 40 Kg/cm$^2$.G at 100° C. The results are shown in Table 3. The yield of the 2,6-naphthalenedicarboxylic acid salt in Table 3 is also based on the amount of B—C charged.

TABLE 3

| Example No. | Kind of aromatic carboxylic acid salt | Yield (%) |
| --- | --- | --- |
| 25 | Dipotassium terephthalate | 30 |
| 26 | Dipotassium isophthalate | 30 |
| 27 | Potassium benzoate | 25 |
| 28 | Tetrapotassium pyromellitate | 49 |

EXAMPLE 29

Dipotassium phthalate was mixed with cadmium iodide and cesium iodide, each in an amount of 16 mole % of the phthalate, and pulverized in a ball mill. An autoclave was charged with 7.0 g of the mixture and 21.0 g of diphenylene oxide, heated to 100° C., flushed with carbon dioxide gas, and then filled with carbon dioxide gas to a pressure of 40 Kg/cm$^2$. G.

The mixture was heated with stirring to 400° C. at a rate of 5° C./minute and stirred at this temperature for 18 hours. Upon completion of the reaction 140 ml of toluene and 140 ml of water were added to the reaction mixture, stirred well, the solids soluble in neither the water nor the toluene were filtered off, and the aqueous layer was separated. The aqueous layer was acidified with hydrochloric acid to precipitate 1.50 g of a mixture of diphenylene oxide carboxylic acids and benzenecarboxylic acids. The mixture was purified by column chromatography (packing; Sephadex LH-20) to isolate the desired diphenylene oxide-2,4,6,8-tetracarboxylic acid (0.60 g).

EXAMPLE 30

Substituting dispotassium naphthalate for the dispotassium phthalate, 10.0 g of the mixture of the dispotassium salt and the catalyst and 30.0 g of diphenylene oxide were submitted to the reaction at 430° C. as in Example 29 to yield 2.03 g of a mixture of diphenylene oxide carboxylic acids and naphthalenecarboxylic acids. The mixture was purified as in Example 29 to isolate 0.61 g of the desired diphenylene oxide-1,3,6,8-tetracarboxylic acid.

EXAMPLE 31

Substituting phenanthrene for the diphenylene oxide, the reaction was carried out and the products were worked up as in Example 29 to yield 0.25 g of a mixture of phenanthrenecarboxylic acids and benzenecarboxylic acids. The mixture was purified as in Example 29 to isolate 40 mg of the desired 2,7-phenanthrenedicarboxylic acid.

EXAMPLE 32

The reaction was carried out and the products were worked up as in Example 29 except that carbazole was substituted for the diphenylene oxide, the raw materials and the catalyst charged into the autoclave were heated to 250° C., and the pressure of carbon dioxide gas was set at 60 Kg/$cm^2$.G. A mixture (1.20 g) of carbazolecarboxylic acids and benzenecarboxylic acids thereby obtained was purified as in Example 29 to isolate 0.44 g of the desired carbozole-1,3,6,8-tetracarboxylic acid.

EXAMPLE 33

Tetrapotassium pyromellitate was mixed with cadmium iodide in an amount of 16 mole % of the pyromellitate and pulverized in a ball mill. An autoclave was charged with 7.00 g of the mixture and 21.0 g of diphenylene oxide, heated to 100° C., flushed with carbon dioxide gas, and then filled with carbon dioxide gas to a pressure of 40 Kg/$cm^2$.G.

The mixture in the autoclave was heated with stirring to 400° C. at a rate of 5° C./minute and stirred at this temperature for 7 hours. Upon completion of the reaction, 140 ml of toluene and 140 ml of water were added to the reaction mixture, stirred well, the solids soluble in neither the water nor the toluene were filtered off, and the aqueous layer was separated. The aqueous layer was acidified with hydrochloric acid to precipitate 2.34 g of a mixture of diphenylene oxide carboxylic acids and benzenecarboxylic acids.

A portion of the mixture was sampled, esterified with diazomethane in the usual manner, and analyzed by mass spectroscopy. The analysis indicated the presence of compounds with molecular weight of 226, 284, 342, 400, and 458 corresponding respectively to monocarboxylic acid monomethyl ester, dicarboxylic acid dimethyl ester, tricarboxylic acid trimethyl ester, tetracarboxylic acid tetramethyl ester, and pentacarboxylic acid pentamethyl ester derived from diphenylene oxide.

The mixture of the carboxylic acids, 2.14 g, was then purified in a column packed with Sephadex LH-20 by elution with a 7:3 mixture of water and methanol to yield 0.75 g of white crystals of pure diphenylene oxide-2,4,6,8-tetracarboxylic acid with a melting point of 300° C. or higher. The infrared absorption spectroscopy (KBr) showed a spectrum with characteristic absorption bands at 3,300–3,450, 1,730, 1,715, 1,700, 1,685, 1,270, 1,190, 765, and 635 $cm^{-1}$. The proton nuclear magnetic resonance ($^1$H-NMR) spectroscopy in deuterated dimethyl sulfoxide (DMSO-$d_6$) at 400 MHz showed a spectrum with signals at 8.67 ppm (2H, d, J=1.0 Hz) and 9.19 ppm (2H, d, J=1.0 Hz) on the $\delta$ scale while the carbon-13 nuclear magnetic resonance ($^{13}$C-NMR) spectroscopy in DMSO-$d_6$ at 100 MHz showed a spectrum with signals at 116.56, 124.81, 126.57, 131.54, 157.11, 164.39, and 166.32 ppm on the $\delta$ scale.

The aforesaid crystals of diphenylene oxide-2,4,6,8-tetracarboxylic acid, 40 mg, were esterified with diazomethane in the usual manner to yield 18 mg of white crystals of the tetramethyl ester. The crystals showed a melting point of 245°–247° C., characteristic infrared absorption bands (KBr) at 3,450, 1,720, 1,275, 1,200, 765, and 645 $cm^{-1}$, and $^1$H-NMR signals [in deuterated chloroform (CDCl$_3$) at 90 MHz] at 4.02 ppm (6H, s), 4.12 ppm (6H, s), and 8.91 ppm (4H, s) on the $\delta$ scale.

EXAMPLE 34

Tetrapotassium pyromellitate was mixed with zinc chloride and potassium iodide, each in an amount of 16 mole % of the pyromellitate, and 7.00 g of the mixture and 21.0 g of diphenylene oxide were charged into an autoclave under carbon dioxide pressure (40 Kg/$cm^2$.G) as in Example 33 heated with stirring to 430° C. at a rate of 5° C./minute, stirred at this temperature for 18 hours, and the reaction mixture was worked up as in Example 33 to yield 3.01 g of a mixture of diphenylene oxide carboxylic acids and benzenecarboxylic acids. The mixture, 2.40 g, was purified in a column packed with Sephadex LH-20 to yield 0.77 g of white crystals of pure diphenylene oxide-2,4,6,8-tetracarboxylic acid.

EXAMPLE 35

Tetrapotassium pyromellitate was mixed with cadmium iodide in an amount of 16 mole % of the pyromellitate and 10.0 g of the mixture, 15.0 g of diphenylene oxide, and 15 g of naphthalene were charged into an autoclave under carbon dioxide pressure (40 Kg/$cm^2$.G) as in Example 33, heated with stirring to 430° C. at a rate of 5° C./minute, stirred at this temperature for 18 hours, and the reaction mixture was worked up with the use of 200 ml of toluene and 200 ml of water as in Example 35 to yield 3.60 g of a mixture of diphenylene oxide carboxylic acids and benzenecarboxylic acids. The mixture, 1.50 g, was purified in a column packed with Sephadex LH-20 to yield 0.77 g of white crystals of pure diphenylene oxide-2,4,6,8-tetracarboxylic acid.

EXAMPLE 36

Tetrapotassium pyromellitate was mixed with cadmium iodide in an amount of 16 mole % of the pyromellitate and 10.0 g of the mixture and 30.0 g of phenanthrene were charged into an autoclave under carbon dioxide pressure as in Example 33, heated with stirring to 400° C. at a rate of 5° C./minute, stirred at this temperature for 18 hours, and the reaction mixture was worked up with the use of 200 ml of toluene and 200 ml of water as in Example 33 to yield 0.99 g of a mixture of phenanthrenecarboxylic acids and benzenecarboxylic acids.

The analysis of a portion of the mixture by mass spectroscoy as in Example 33 indicated the presence of compounds with molecular weight of 236, 294, and 352 corresponding respectively to phenanthrenemonocarboxylic acid monomethyl ester, pheneanthrenedicarboxylic acid dimethyl ester, and phenanthrenetricarboxylic acid trimethyl ester.

The aforesaid mixture of the carboxylic acids, 0.30 g, was purified in a column packed with Sephadex LH-20 by elution with a 7:3 mixture of water and methanol to yield 0.12 g of white crystals of pure phenanthrene-2,7-dicarboxylic acid with a melting point of 300° C. or higher. The infrared spectrum (KBr) showed characteristic absorption bands at 2,600–2,900, 1,685, 1,410, 1,290, 1,215, 750, and 730 $cm^{-1}$, the $^1$H-NMR spectrum (DMSO-d$_6$, 90 MHz) showed signals at 8.19 ppm (2H, s), 8.23 ppm (2H, dd, J=2, 9H), 8.68 ppm (2H, d, J=2 Hz), and 9.00 ppm (2H, d, J=9 Hz) on the δ scale, and the $^{13}$C-NMR spectrum (DMSO-d$_6$, 22.5 MHz) showed signals at 112.66, 119.96, 123.96, 125.70, 126.35, 127.87, and 163.08 ppm on the δ scale.

The aforesaid crystals of phenanthrene-2,7-dicarboxylic acid, 48 mg, were esterified with diazomethane in the usual manner to yield 29 mg of the dimethyl ester with a melting point of 204°–205° C. The infrared spectrum (KBr) showed characteristic absorption bands at 3,400, 2,900, 1,720, 1,425, 1,280, 1,200, and 745 cm$^{-1}$, and the $^1$H-NMR spectrum (CDCl$_3$, 90 MHz) showed signals at 4.01 ppm (6H, s), 7.82 ppm (2H, s), 8.24 ppm (2H, dd, J=9 Hz), 8.59 ppm (2H, d, J=2 Hz), and 8.96 ppm (2H, d, J=9 Hz) on the δ scale.

EXAMPLE 37

Tetrapotassium pyromellitate was mixed with cadmium iodide in an amount of 16 mole % of the pyromellitate and pulverized in a ball mill. An autoclave was charged with 7.00 g of the mixture and 21.0 g of carbazole, heated to 250° C., flushed with carbon dioxide gas, and then filled with carbon dioxide gas to a pressure of 55 Kg/cm$^2$.G.

The mixture was heated with stirring to 400° C. at a rate of 5° C./minute, stirred at this temperature for 8 hours, and the reaction mixture was worked up with the use of 140 ml of toluene and 140 ml of water as in Example 33 to yield 3.31 g of a mixture of carbazolecarboxylic acids and benzenecarboxylic acids.

The analysis of a portion of the mixture by mass spectroscopy as in Example 33 indicated the presence of compounds with molecular weight of 225, 283, 341, and 399 corresponding respectively to carbazolemonocarboxylic acid monomethyl ester, carbazoledicarboxylic acid dimethyl ester, carbazoletricarboxylic acid trimethyl ester, and carbozoletetracarboxylic acid tetramethyl ester.

The mixture of the carboxylic acids, 0.61 g, was purified in a column packed with Sephadex LH-20 by elution with a 7:3 mixture of water and methanol to give 0.21 g of pale yellow crystals of pure carbazole-1,3,6,8-tetracarboxylic acid with a melting point of 300° C. or higher. The infrared spectrum (KBr) showed characteristic absorption bands at 3,400, 3,050–2,850, 1,725, 1,680, 1,435, 1,405, 1,205, 760, and 720 cm$^{-1}$, the $^1$H-NMR spectrum (DMSO-d$_6$, 90 MHz) showed signals at 8.67 ppm (2H, d, J=1.5 Hz) and 9.20 ppm (2H, d, J=1.5 Hz), and the $^{13}$C-NMR spectrum (DMSO-d$_6$, 22.5 MHz) showed signals at 109.3, 119.0, 119.5, 123.5, 125.9, 138.0, 162.9, and 163.0 ppm on the δ scale.

The aforesaid crystals of carbazole-1,3,6,8-tetracarboxylic acid, 45 mg, were esterified with diazomethane in the usual manner to yield 25 mg of the dimethyl ester with a melting point of 245°–247° C. The infrared spectrum (KBr) showed characteristic absorption bands at 3,400, 2,950, 1,705, 1,430, 1,270, 1,240, 760, and 725 cm$^{-1}$ and the $^1$H-NMR spectrum (CDCl$_3$, 90 MHz) showed signals at 4.01 ppm (6H, s), 4.08 ppm (6H, s), 8.74 ppm (2H, d, J=1.7 Hz), and 8.85 ppm (2H, d, J=1.7 Hz) on the δ scale.

EXAMPLE 38

Tetrapotassium pyromellitate was mixed with zinc chloride and potassium iodide, each in an amount of 16 mole % of the pyromellitate, 7.00 g of the mixture and 21.0 g of carbazole were charged into an autoclave under carbon dioxide pressure (40 Kg/cm$^2$.G) as in Example 37, heated with stirring to 430° C. at a rate of 5° C./minute, stirred at this temperature for 18 hours, and the reaction mixture was worked up as in Example 37 to yield 0.92 g of a mixture of carbazolecarboxylic acids and benzenecarboxylic acids. The mixture, 0.50 g, was purified in a column packed with Sephadex LH-20 to yield 90 mg of pale yellow crystals of pure carbazole-1,3,6,8-tetracarboxylic acid.

EXAMPLE 39

Tetrapotassium pyromellitate was mixed with zinc chloride and potassium iodide, each in an amount of 16 mole % of the pyromellitate, 10.0 g of the resulting mixture, 15.0 g of carbazole, and 15 g of naphthalene were charged into an autoclave under dioxide pressure (40 Kg/cm$^2$.G) as in Example 37, heated with stirring to 400° C. at a rate of 5° C./minute, stirred at this temperature for 18 hours, and the reaction mixture was worked up with the use of 200 ml of toluene and 200 ml of water as in Example 37 to yield 4.12 g of a mixture of carbazolecarboxylic acids and benzenecarboxylic acids. The mixture, 1.20 g, was purified in a column packed with Sephadex LH-20 to yield 0.34 g of pale yellow crystals of pure carbazole-1,3,6,8-tetracarboxylic acid.

EXAMPLES 40–46

Using naphthalene, diphenylene oxide, phenanthrene, or carbazole as aromatic compound, dipotassium phthalate as aromatic carboxylic acid salt, and thallium iodide alone or in admixture with cesium iodide as catalyst, the reaction was carried out at the temperature shown in Table 4 and the reaction mixture was worked up as in the preceding examples to produce 2,6-naphthalenedicarboxylic acid, diphenylene oxide-1,3,6,8-tetracarboxylic acid, phenanthrene-2,7-dicarboxylic acid, or carbazole-2,4,6,8-tetracarboxylic acid in the yield shown in Table 4.

TABLE 4

| Example No. | Kind of aromatic compound | Kind of catalyst | Reaction Temperature (°C.) | Product Kind | Yield |
|---|---|---|---|---|---|
| 40 | NA | TlI | 400 | NDCA | 1 |
| 41 | " | " | 430 | " | 5 |
| 42 | " | TlI + CsI | 400 | " | 8 |
| 43 | " | TlI + CsI | 430 | " | 16 |
| 44 | DPO | TlI | " | DTCA | 0.49 |
| 45 | PH | " | " | PDCA | 0.17 |
| 46 | CB | " | " | CTCA | 1.44 |

(Notes)
NA: Naphthalene
DPO: Diphenylene oxide
PH: Phenanthrene
CB: Carbazole
NDCA: 2,6-Naphthalenedicarboxy acid
DTCA: Diphenylene oxide-2,4,6,8-tetracarboxylic acid
PDCA: Phenanthrene-2,7-dicarboxylic acid
CTCA: Carbazole-1,3,6,8-tetracarboxylic acid
Yield: % by mole in Examples 40–43 and grams in Examples 44–46

What is claimed is:

1. A process for the preparation of aromatic carboxylic acids which comprises heating carboxyl-free aromatic compounds and aromatic carboxylic acid salts, said salts differing when stripped of their carboxyl groups from said aromatic compounds in their basic structure, under carbon dioxide pressure of 10 to 200 kg/cm$^2$.G at a temperature of 300° to 500° C., in the presence of a catalytic amount of one or more metal compounds selected from group (a) of compounds of zinc, cadmium, and thallium, and one or more compounds selected from group (b) of compounds of cesium, Group IIa metals, and Group IIIa metals selected from the group consisting of scandium, yttrium and lanthanides to produce carboxylic acids or their salts containing the ring structure of said carboxyl-free aromatic compounds.

2. A process for the preparation of aromatic carboxylic acids according to claim 1 wherein the carboxyl-free aromatic compounds is naphthalene.

3. A process for the preparation of aromatic carboxylic acids according to claim 1 wherein the carboxyl-free aromatic compounds is a polycyclic aromatic compounds with three or more rings.

4. A process for the preparation of aromatic carboxylic acids according to claim 3 wherein the polycyclic aromatic compound is diphenylene oxide, phenanthrene, or carbazole.

5. A process for the preparation of aromatic carboxylic acids according to claim 1 wherein the aromatic carboxylic acid salt is the potassium salt or sodium salt of an aromatic carboxylic acid.

6. A process for the preparation of aromatic carboxylic acids according to claim 1 wherein the aromatic carboxylic acid salt is the salt of a monocyclic or bicyclic aromatic carboxylic acid.

7. A process for the preparation of aromatic carboxylic acids according to claim 1 wherein the compounds of the Group IIIa metals are the compounds of lanthanides.

8. A process for the preparation of aromatic carboxylic acids according to claim 1 wherein the carboxyl-free aromatic compound is a polycyclic aromatic compound with three or more rings and the aromatic carboxylic acid salt is the salt of a monocyclic or bicyclic aromatic carboxylic acid.

9. A process for the preparation of aromatic carboxylic acids which comprises heating carboxyl-free polycyclic aromatic compounds with three or more rings and mono- or di-cyclic aromatic acid salts under carbon dioxide pressure in the presence of a catalytic amount of one or more metal compounds selected from group (a) of compounds of zinc, cadmium, and thallium, and one or more compounds selected from the group (b) of cesium, Group IIa metals, and Group IIIa metals selected from the group consisting of scandium, yttrium, and lanthanides, to produce carboxylic acids or their salts containing the ring structure of said polycyclic aromatic compounds.

10. A process for the preparation of aromatic carboxylic acids according to claim 9, wherein the polycyclic aromatic compound is diphenylene oxide, phenanthrene, or carbazole.

11. A process for the preparation of aromatic carboxylic acids which comprises heating carboxyl-free aromatic compounds and aromatic carboxylic acid potassium salts, said salts differing when stripped of their carboxyl groups from said aromatic compounds in their basic structure, under carbon dioxide pressure of 10 to 200 kg/cm$^2$.G at 300° to 500° C. in the presence of a catalyst comprising at least one cesium compound and at least one cerium compound to produce carboxylic acids or their salts containing the ring structure of said carboxyl-free aromatic compounds.

* * * * *